United States Patent
Silverman et al.

(10) Patent No.: US 7,056,277 B2
(45) Date of Patent: *Jun. 6, 2006

(54) METHOD FOR TREATING TISSUE WITH AN IMPLANT

(75) Inventors: David E. Silverman, Palo Alto, CA (US); Alan Stein, Moss Beach, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 95 days.

This patent is subject to a terminal disclaimer.

(21) Appl. No.: 10/455,683

(22) Filed: Jun. 4, 2003

(65) Prior Publication Data

US 2003/0199730 A1    Oct. 23, 2003

Related U.S. Application Data

(63) Continuation of application No. 09/852,403, filed on May 9, 2001, now Pat. No. 6,595,909, which is a continuation of application No. 09/447,663, filed on Nov. 23, 1999, now Pat. No. 6,251,064, and a continuation-in-part of application No. 09/286,245, filed on Apr. 5, 1999, now Pat. No. 6,251,063, which is a continuation-in-part of application No. 09/232,056, filed on Jan. 15, 1999, now Pat. No. 6,238,335.

(60) Provisional application No. 60/149,569, filed on Aug. 18, 1999, provisional application No. 60/111,884, filed on Dec. 11, 1998.

(51) Int. Cl.
*A61F 2/00* (2006.01)

(52) U.S. Cl. ...................................... 600/29

(58) Field of Classification Search ............ 600/29–30; 424/93.7, 423, 551; 128/898; 623/11.11, 623/23.65, 23.66
See application file for complete search history.

(56) References Cited

U.S. PATENT DOCUMENTS

| | | | |
|---|---|---|---|
| 3,094,122 A | 6/1963 | Gauthier et al. |
| 3,204,634 A | 9/1965 | Koehn |
| 4,271,827 A | 6/1981 | Angelchik |
| 4,351,333 A | 9/1982 | Lazarus et al. |
| 4,424,208 A | 1/1984 | Wallace et al. |
| 4,582,640 A | 4/1986 | Smestad et al. |
| 4,773,393 A | 9/1988 | Haber et al. |
| 4,803,075 A | 2/1989 | Wallace et al. |
| 4,837,285 A | 6/1989 | Berg et al. |
| 5,007,940 A | 4/1991 | Berg |
| 5,067,965 A | 11/1991 | Ersek et al. |
| 5,116,387 A | 5/1992 | Berg |
| 5,158,573 A | 10/1992 | Berg |
| 5,204,382 A | 4/1993 | Wallace et al. |
| 5,258,028 A | 11/1993 | Ersek et al. |

(Continued)

FOREIGN PATENT DOCUMENTS

AU        A-34223/95        5/1996

(Continued)

OTHER PUBLICATIONS

New Riverside University Dictionary, 1984; The Riverside Publishing Company; pp. 774-775, 778, 1154.*

(Continued)

*Primary Examiner*—John P. Lacyk
(74) *Attorney, Agent, or Firm*—Dorsey & Whitney LLP (57) ABSTRACT

A method for creating an implant in a wall forming a cavity in a mammalian body and having a muscle layer extending circumferentially around the cavity. A material is introduced into the wall so that the material extends along the muscle layer to form an implant in the wall.

19 Claims, 4 Drawing Sheets

U.S. PATENT DOCUMENTS

| | | | |
|---|---|---|---|
| 5,301,682 | A | 4/1994 | Debbas |
| 5,314,473 | A | 5/1994 | Godin |
| 5,336,263 | A | 8/1994 | Ersek et al. |
| 5,451,406 | A | 9/1995 | Lawin et al. |
| 5,480,644 | A | 1/1996 | Freed |
| 5,490,984 | A | 2/1996 | Freed |
| 5,580,568 | A | 12/1996 | Greff et al. |
| 5,667,767 | A | 9/1997 | Greff et al. |
| 5,667,778 | A * | 9/1997 | Atala .................. 424/93.7 |
| 5,695,480 | A | 12/1997 | Evans et al. |
| 5,755,658 | A | 5/1998 | Wallace et al. |
| 5,785,642 | A | 7/1998 | Wallace et al. |
| 5,792,478 | A | 8/1998 | Lawin et al. |
| 5,830,178 | A | 11/1998 | Jones et al. |
| 5,855,615 | A | 1/1999 | Bley et al. |
| 5,861,036 | A | 1/1999 | Godin |
| 6,099,567 | A * | 8/2000 | Badylak et al. .......... 623/11.11 |
| 6,238,335 | B1 * | 5/2001 | Silverman et al. ............ 600/29 |
| 6,251,063 | B1 * | 6/2001 | Silverman et al. ............ 600/29 |
| 6,251,064 | B1 | 6/2001 | Silverman et al. |
| 6,335,028 | B1 * | 1/2002 | Vogel et al. ................ 424/422 |
| 6,576,019 | B1 * | 6/2003 | Atala ....................... 623/23.65 |
| 6,591,838 | B1 * | 7/2003 | Durgin ....................... 128/898 |
| 6,595,909 | B1 * | 7/2003 | Silverman et al. ............ 600/29 |

FOREIGN PATENT DOCUMENTS

| | | |
|---|---|---|
| WO | WO 97/19643 | 6/1997 |
| WO | WO 97/45131 | 12/1997 |
| WO | WO 98/01088 | 1/1998 |
| WO | WO 98/17200 | 4/1998 |
| WO | WO 98/17201 | 4/1998 |

OTHER PUBLICATIONS

Aye, R. W. et al., "Early Results With the Laparoscopic Hill Repair", (May 1994), *Am. Jrnl. of Surgery*, vol. 167, pp. 542-546.

Collard, J.M. et al., "Laparoscopic Antireflux Surgery/What is Real Progress?", (1994), *Annals of Surgery*, vol. 220, No. 2, pp. 146-154.

DeMeester, T.R. et al., "Nissen Fundoplication for Gastroesophageal Reflux Disease", (1986), *Annals of Surgery*, vol. 204, No. 1, pp. 9-20.

Donahue, P.E. et al., "The Floppy Nissen Fundoplication/Effective Long-term Control of Pathologic Reflux", (Jun. 1985), *Arch Surg*, vol. 120, pp. 663-668.

Ellis, Jr., F.H., "The Nissen Fundoplication", (1992), *Ann. Thorac. Surg.*, vol. 54, pp. 1231-1235.

Grande, L. et al., "Value of Nissen fundoplication in patients with gastro-oesophageal reflux judged by long-term sympton control", (1994), *Brit, Jnl. of Surgery*, vol. 81, pp. 548-550.

Hill, L.D. et al., "Laparoscopic Hill Repair", (Jan. 1994), *Contemporary Surgery*, vol. 44, No. 1, pp. 13-20.

Hunter, J.G. et al., "A Physiologic Approach to Laparoscopic Fundoplication for Gastroesophageal Reflux Disease", (1996), *Annals of Surgery*, vol. 223, No. 6, pp. 673-687.

Ireland, A.C. et al., "Mechanisms undrlying the antireflux action of fundoplication", (1993), *Gut*, vol. 34, pp. 303-308.

Johansson, J. et al., "Outcome 5 years after 360' fundoplication for gastro-oesophageal reflux disease", (Jan. 1993), *Brit. Jnl. of Surgery*, vol. 80, pp. 46-49.

Kauer, W.K.H. et al., "Mixed Reflux of Gastric and Duodenal Juices Is More Harmful to the Esophagus than Gastric Juice Alone/The Need for Surgical Therapy Re-Emphasized", (1995) *Annals of Surgery*, vol. 222, No. 4, pp. 525-533.

Klingman, R.R. et al., "The Current Management of Gastroesophageal Reflux", (1991), *Adv. Surg.*, vol. 24, pp. 259-291.

Little, A.G., "Mechanisms of Action of Antireflux Surgery: Theory and Fact", (1992), *World Jnl. of Surgery*, vol. 16, pp. 320-325.

Luostarinen, M., "Nissen Fundoplication for Reflux Esophagitis/Long-Term Clinical and Endoscopic Results in 109 of 127 Consecutive Patients", (1993), *Annals of Surgery*, vol. 217, No. 4, pp. 329-337.

Luostarinen, M. et al., "Fate of Nissen fundoplication after 20 years. A clinical, endoscopical, and functional analysis", (1993), *Gut*, vol. 34, pp. 1015-1020.

Malizia, A. et al., "Migration and Granulomatous Reaction After Periurethral injection of Polytef (Teflon)", (Jun. 1984), *JAMA*, vol. 251, No. 24, pp. 3277-3281.

Martin, C. et al., "Collis-Nissen Gastroplasty Fundoplication For Complicated Gastro-Oesophageal Reflux Disease", (1992), *Aust. N.Z. Jnl. Surg.*, vol. 62, pp. 126-129.

O'Connor, K.W. et al., "Endoscopic placement of collagen at the lower esophageal sphincter to inhibit gastroesophageal reflux: a pilot study of 10 medically intractable patients", (1988), *Gastrointestinal Endoscopy*, vol. 34, No. 2, pp. 106-112.

O'Connor, K. W. et al., "An experiemtnal endoscopic technique for reversing gastroesophageal reflux in dogs by injecting inert material in the distal esophagus", (1984) Gastrointestinal Endoscopy, vol. 30, No. 5, pp. 275-280.

Ortiz, A. et al., "Conservative treatment versus antireflux surgery in Barrett's oesophagus: long-term results of a prospective study", (1996), *Brit. Jnl. of Surg.*, vol. 83, 274-278.

Politano, V. et al., "Periurethral Teflon Injection for Urinary Incontinence", (Feb. 1974) *Jnl.Urology*, vol. 111, pp. 180-183.

Pope, C., "The Quality of Life Following Antireflux Surgery", (1992), *World Jnl. of Surgery*, vol. 16, pp. 355-358.

Schulman, C.C. et al., "Endoscopic injections of Teflon to treat urinary incontinence in women", (Jan. 21, 1984) *BMJ*, vol. 228, p. 192.

Shafik, A., "Intraesophageal Polytef injection for the treatment of reflux esophagitis", (1996), *Surgical Endoscopy*, pp. 329-331.

Shirazi, S.S. et al., "Long-term Follow-up for Treatment of Complicated Chronic Reflux Esophagitis", (May 1987), *Arch Surg*, vol. 122, 548-552.

Society of Am. Gastrointestinal Endoscopic Surgeons, Los Angeles, CA, "Granting of Privileges for Laparascopic General Surgery", (Mar. 1991), *Am. Jrnl. of Surgery*, vol. 161, pp. 324-325.

Spechler, S.J. et al., "Comparison of Medical and Surgicl Therapy for Complicated Gastroesophageal Reflux Disease in Veterans", (Mar. 19, 1992), *NE Jnl. of Med*, vol. 326, No. 12, pp. 786-792.

Spechler, S.J. et al., "The Columnar-Lined Esophagus, Intestinal Metaplasia, and Norman Barrett", (1996), *Gastroenterology*, vol. 110, pp. 614-621.

Thor, K.B. et al., "A Long-Term Randomized Prospective Trial of the Nissen Procedure Versus a Modified Toupet Technique", (Dec. 1989), *Ann. Surg.*, vol. 210, No. 6, pp. 719-724.

Vaezi, M.F. et al., "Synergism of acid and duodenogastroesophageal reflux in complicated Barrett's esophagus", (1995), *Surgery*, vol. 117, pp. 699-704.

Walker, R.D. et al., "Injectable Bioglass as a Potential Substitute for Injectable Polytetrafluoroethylene", (Aug. 1992), *J. Urol.*, vol. 148, pp. 645-647.

Waring, J.P. et al., "The Preoperative Evaluation of Patients Considered for Laparoscopic Antireflux Surgery", (1995), *Am. Jnl. Of Gastroenterology*, vol. 90, No. 1, pp. 35-38.

* cited by examiner

METHOD FOR TREATING TISSUE WITH AN IMPLANT

This application is a continuation application of U.S. utility patent application Ser. No. 09/852,403 filed May 9, 2001, now U.S. Pat. No. 6,595,909, which is a continuation application of U.S. patent application Ser. No. 09/447,663 filed Nov. 23, 1999, now U.S. Pat. No. 6,251,064, which claims the benefit of U.S. provisional patent application Ser. No. 60/149,569 filed Aug. 18, 1999 and is a continuation-in-part of U.S. patent application Ser. No. 09/286,245 filed Apr. 5, 1999, now U.S. Pat. No. 6,251,063, which is a continuation-in-part of U.S. patent application Ser. No. 09/232,056 filed Jan. 15, 1999, now U.S. Pat. No. 6,238,335, and claims the benefit of U.S. provisional patent application Ser. No. 60/111,884 filed Dec. 11, 1998, the entire contents of each of which are incorporated herein by this reference.

This invention pertains to the treatment of the gastrointestinal tract, and more particularly, to the formation of implants in the wall forming the gastrointestinal tract.

U.S. Pat. No. 6,251,063 describes a method and device for augmenting or bulking gastrointestinal tract walls by injecting at least one nonaqueous material into the walls in order to form one or more nonbiodegradable solid implants therein. There is a need for a method for more predictably forming and placing implants in gastrointestinal tract walls which are more clinically efficacious.

In general, it is an object of the present invention to provide a method for creating a valve-like mechanism in a natural body passageway.

Another object of the invention is to provide a method of the above character in which at least one implant is formed in the wall forming the natural body passageway.

Another object of the invention is to provide a method of the above character in which a plurality of circumferentially disposed implants are formed in the wall forming the natural body passageway.

Another object of the invention is to provide a method of the above character in which an arcuate implant extending circumferentially around at least a portion of the natural body passageway is formed.

Another object of the invention is to provide a method of the above character in which a ring-like implant is formed in the wall forming the natural body passageway.

Another object of the invention is to provide a method of the above character for enhancing the lower esophageal sphincter.

Additional objects and features of the invention will appear from the following description from which the preferred embodiments are set forth in detail in conjunction with the accompanying drawings.

In general, a method for forming a valve-like mechanism in a body of a mammal having an esophagus extending through a lower esophageal sphincter to a stomach and formed by a wall having a muscle layer and a mucosal layer is provided. At least one implant is formed in the muscle layer of the wall in the vicinity of the lower esophageal sphincter. The implant inhibits opening of the esophagus at the lower esophageal sphincter and causes the mucosal layer to appose in the vicinity of the implants.

Figures 1, 2, 4:
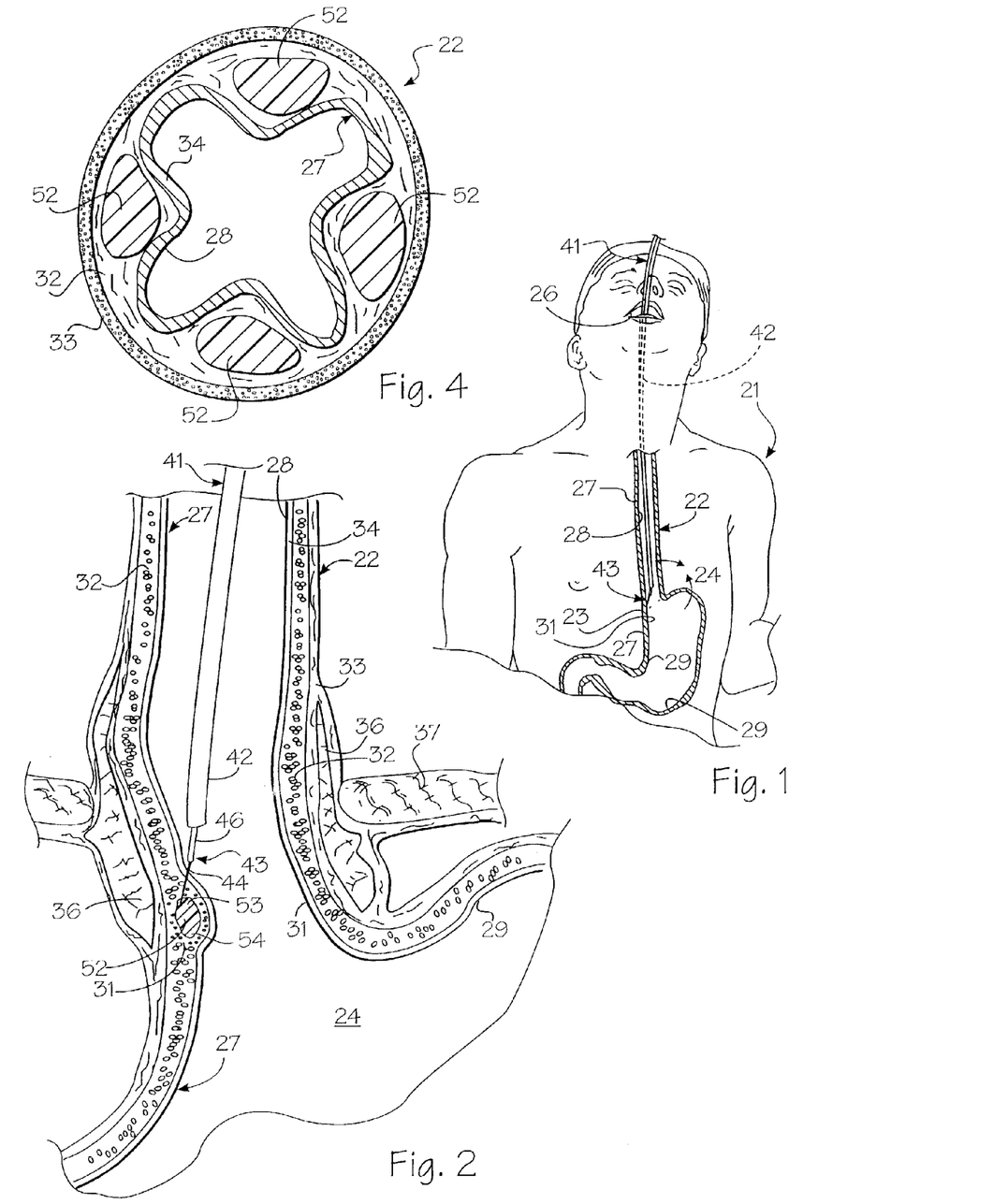
FIG. 1 is a schematic view with the device in place in the stomach and lower esophagus for treatment by the method of the present invention.
FIG. 2 is a cross-sectional view of the lower portion of the esophagus and a portion of the stomach with the device in place and an implant formed by the method of the present invention.
FIG. 4 is a cross-sectional view taken along the line 4—4 of FIG. 3.

The method of the present invention is for use in a natural body cavity such as the gastrointestinal tract in a body of a mammal. A portion of a human body 21 is shown in FIG. 1 and has an internal cavity in the form of the passage of the esophagus 22 extending through a lower esophageal sphincter 23 to a stomach 24. Such cavity is accessible by a natural body opening in the form of mouth 26 and is defined by wall 27. Esophagus 22 is part of the gastrointestinal tract of body 21 that extends from mouth 26 to an anus (not shown).

Esophageal mucosa 28 serves as the inner layer of the intraluminal wall 27 in esophagus 22 and the gastric mucosa 29 serves as the inner layer of the intramural wall 27 in stomach 24. Esophageal mucosa 28 and gastric mucosa 29 meet at the squamous columnar junction 31. Wall 27 has a muscle layer comprising layer of circular muscle 32 extending beneath mucosa layers 28 and 29 and layer of longitudinal muscle 33 beneath circular muscle 32. Muscle layers 32 and 33 each extend around esophagus 22 and stomach 24. Wall 27 further includes a submucosal layer or submucosa 34 extending between the mucosa and the muscle layers. A submucosal space, that is a potential space, can be created between mucosal layer 28 or 29 and circular muscle layer 32 by the separation of layer 28 or 29 from muscle layer 32. In addition, as with any muscle, wall 27 includes an intramuscular potential space, that is a space which can be created intramuscularly by distension and separation of muscle fibers within a single muscle. Wall 27 has a depth or thickness which includes at least mucosal layers 28 and 29, muscle layers 32 and 33 and the submucosal layer 34. The phreno-esophageal ligament 36 and diaphragm 37 extend around esophagus 22 above the lower esophageal sphincter 23.

The method of the present invention can be performed with any of the apparatus disclosed in U.S. Pat. Nos. 6,251,063 and 6,238,335. In general, a suitable apparatus or medical device 41 includes a probe member or probe 42 having an optical viewing device. A conventional or other suitable gastroscope or endoscope can be used for probe 42. An exemplary probe is an Olympus CF Type 40L/I endoscope made by Olympus Corporation of Tokyo, Japan. A needle assembly 43 is slidably carried by probe 42. Needle assembly 43 can be of any conventional type, such as a modified sclerotherapy needle similar to the Bard® Flex-itip™ needle manufactured by C.R. Bard, Inc. of Billerica, Md., and includes a needle member or needle 44 and protective sleeve 46. Device 41 further includes a supply assembly (not shown) mounted to the proximal end portion of needle assembly 43. The supply assembly is secured to the proximal extremity of needle assembly 43 and can include a conventional syringe for introducing a liquid or solution through needle 44. The supply assembly optionally includes second and third reservoirs in the form of second and third syringes. The second syringe is filled with dimethyl sulfoxide (DMSO) or any other suitable liquid. The third syringe is filled with a saline solution or any other suitable aqueous or physiological solution.

In the method of the present invention, at least one implant forming, solution is introduced into the wall 27 of the gastrointestinal tract to form at least one implant in the wall 27 of the gastrointestinal tract. Any suitable material, from which an implant can be formed when the fluid, separately or in conjunction with another fluid, is introduced into the body can be used with the method of the present invention. Although aqueous or non-aqueous solutions are amongst the fluids that can be used, an inert, nonresorbable material is preferred. One such material comprises at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a nonaqueous solution which can be introduced into the body as a liquid and from which a solid thereafter precipitates. A preferred embodiment of such a nonaqueous solution is a solution of a biocompatible polymer and a biocompatible solvent which can optionally include a contrast agent for facilitating visualization of the solution in the body.

A particularly preferred implant forming solution is a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 µm or less. It should be appreciated that any percents stated herein which include a contrast agent would be proportionally adjusted when the contrast agent is not utilized. Any contrast agent is preferably a water insoluble biocompatible contrast agent. The weight percent of the polymer, contrast agent and biocompatible solvent is based on the total weight of the complete composition. In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol, ethyl lactate or acetone.

The term "biocompatible polymer" refers to polymers which, in the amounts employed, are non-toxic, chemically inert, and substantially non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly($C_1$–$C_6$) acrylates, acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymers of styrene/maleic acid, and mixtures thereof. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatible polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly($C_1$–$C_6$) acrylates, acrylate copolymers, polyalkyl alkacrylates wherein the alkyl and alk groups independently contain one to six carbon atoms, cellulose acetate butyrate, nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams per milliliter at 20° C.) and include tantalum, tantalum oxide and barium sulfate, each of which is commercially available in the proper form for in vivo use and preferably having a particle size of 10 μm or less. Other water insoluble contrast agents include gold, tungsten and platinum powders. Methods for preparing such water insoluble biocompatible contrast agents having an average particle size of about 10 μm or less are described below. Preferably, the contrast agent is water insoluble (i.e., has a water solubility of less than 0.01 mg/ml at 20° C.)

The contrast agent can be encapsulated in the precipitate, particularly in the water insoluble contrast agent. However, such encapsulation is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The compositions employed in the methods of this invention are prepared by conventional methods whereby each of the components is added and the resulting composition mixed together until the overall composition is substantially homogeneous. For example, sufficient amounts of the selected polymer are added to the biocompatible solvent to achieve the effective concentration for the complete composition. Preferably, the composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

Sufficient amounts of the contrast agent are then optionally added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the non-aqueous solution, the biocompatible polymer composition can be replaced with a biocompatible prepolymer composition containing a biocompatible prepolymer. In this embodiment, the composition comprises a biocompatible prepolymer, an optional biocompatible water insoluble contrast agent preferably having an average particle size of about 10 μm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms a biocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

When the prepolymer is liquid (as in the case of polyurethanes), the use of a biocompatible solvent is not absolutely necessary but may be preferred to provide for an appropriate viscosity in the nonaqueous solution. Preferably, when employed, the biocompatible solvent will comprise from about 10 to about 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Specific embodiments of nonaqueous solutions suitable for use in the apparatus and methods of the invention are described in U.S. Pat. No. 5,667,767 dated Sep. 16, 1997, U.S. Pat. No. 5,580,568 dated Dec. 3, 1996 and U.S. Pat. No. 5,695,480 dated Dec. 9, 1997 and International Publication Number WO 97/45131 having an International Publication Date of Dec. 4, 1997, the entire contents of which are incorporated herein by this reference.

Use of the method of the present invention to create a valve-like mechanism in a human esophagus may be described as follows. Let it be assumed that in preparing for the valve-like forming procedure, the gastrointestinal tract of a patient has previously been evaluated by using any or all techniques and procedures available in the art including, but not limited to, upper gastrointestinal radiographic studies, esophageal endoscopy with biopsies and esophageal motility studies. Assuming that the patient's pretreatment evaluation diagnoses gastroesophageal reflux which warrants the procedure hereinafter described, the patient can be brought into an outpatient clinic or an operating room in a hospital. The patient is preferably placed in a semi-recumbent or lateral decubitus position on an operating or examining table or on a gurney.

After intravenous access has been accomplished and the patient has been appropriately sedated or anesthetized, the distal extremity of probe 42 is introduced through mouth 26 of the patient into esophagus 22. In this regard, the handle of probe 42 is grasped by the physician to introduce the distal extremity of probe 42 into mouth 26 and advance it down esophagus 22 to the vicinity of the area to be treated. The optical viewing device facilities advancement by the physician of probe 42.

The distal end portion of needle assembly 43 is introduced through probe 42 and advanced until the distal end portions of needle 44 and sleeve 46 are in the vicinity of the distal extremity of probe 42. Under the guidance of the optical viewing device, the distal extremity of the probe 42 is maneuvered to a position above the portion of wall 27 which is to be treated. In a preferred method, the distal extremity of probe 42 is positioned in the vicinity of lower esophageal sphincter 23. The physician retracts sleeve 46 relative to needle 44 so that the distal end portion of needle 44 extends beyond the distal end portion of sleeve 46 a desired amount. The physician primes needle 44 with the saline or other aqueous or physiologic solution.

After the physician penetrates wall 27 with the sharpened end of needle 44, in one of the methods of the invention a saline solution can be injected into wall 27 and more specifically into one of muscle layers 32 or 33 or between the layers 32 and 33. The saline injection creates an enlargement in wall 27 having an internal space filled with the saline solution. The amount of injected saline solution can range from 0.25 to 10 cc and preferably ranges from 1 to 3 cc.

After creation of the saline-filled enlargement, the physician retracts needle 44 from wall 27, withdraws the remaining saline solution from the needle passage and cleanses the needle passage with DMSO to ensure that the saline solution has been removed from the passage. Removal of the saline solution from the needle passage and the cleansing of the passage with DMSO inhibits premature precipitation within syringe of the biocompatible polymer in the implant forming solution from the DMSO in the implant forming solution. The needle passage is next primed with the implanting forming solution.

The physician causes the distal end portion of needle 44 to penetrate the enlargements and extend into the saline filled space therein. Thereafter, the physician causes a preselected amount of the implant forming solution to be introduced through needle 44. The optional contrast agent within the implanting forming solution permits the viewing of the solution by means of fluoroscopy. In addition, the introduction of the implant forming solution into wall 27 can be monitored by transabdominal ortransesophageal ultrasound. The rate of injection of the implant forming solution into the space can range from 0.1 cc per minute to 10 cc per minute.

Once the implant forming solution has been introduced into wall 27, the biocompatible polymer of the implant forming solution precipitates to form one or more discrete deposits or solid implants 52 (see FIGS. 2 and 4). The amount of implant forming solution injected into wall 27 for each implant 52 can range from 0.05 cc to 10 cc. The ratio of implant forming solution to saline in the space can range from 2:1 to 1:8 and preferably ranges from approximately one part implant forming solution to two to three parts saline solution. In one embodiment, the space created by the saline solution predefines the configuration of the precipitant or implant 52. The discrete implant 52 can occupy less than all of the space or, alternatively, more implant forming solution than saline can be introduced into wall 27 so that the discrete implant 52 more than fills the space created by the saline.

After completion of the injection of implant forming solution and the solidification of the biocompatible polymer, the remaining solution within the space disperses within body 21 and the space contracts about implant 52.

A plurality of implants 52 are preferentially created in wall 27 in the method of the invention. The number and configuration of implants 52 formed in wall 27 can vary. In one preferred method of the invention, a plurality of implants 52 are created in wall 27 in the vicinity of the lower esophageal sphincter 23. The implants 52 are each somewhat pillow-like in shape and are preferably circumferentially spaced-apart or disposed around the periphery of the esophagus. More specifically, implants 52 are disposed substantially in a plane extending perpendicularly to a longitudinal axis extending along the centerline of esophagus 22. An exemplary rosette of four implants 52 spaced-apart around the center of the rosette at approximately 90° intervals is shown in FIG. 4. It should be appreciated, however, that less than four or greater than four implants 52 can be provided and formed in wall 27 and can be circumferentially spaced-apart at approximately equal angular intervals or asymmetrically disposed about the center line of esophagus 22. Implants 52 which merge with adjacent implants 52 in wall 27 are within the scope of the present invention.

Figure 3:
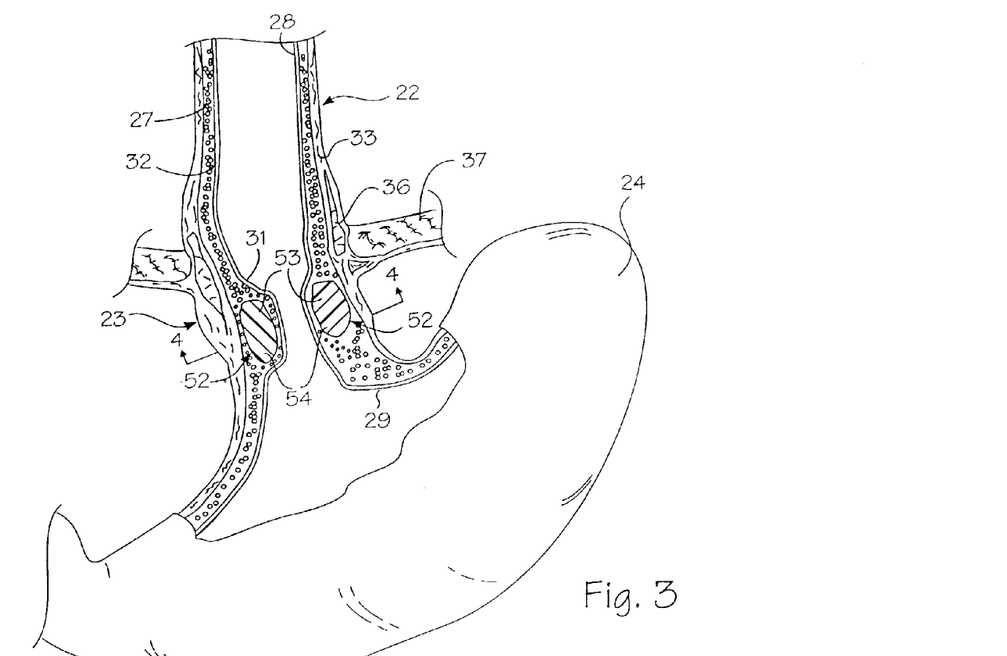
FIG. 3 is a frontal view partially in section of the lower esophagus and a non-distended stomach with implants as treated by the method of the present invention.
Figure 5:
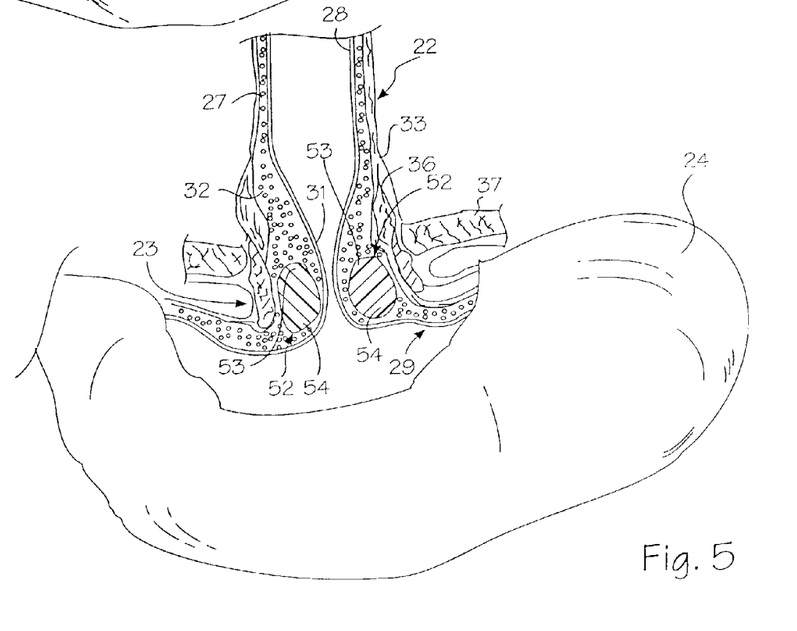
FIG. 5 is a frontal view partially in section of the lower esophagus and distended stomach with implants treated by the method of the present invention.
Figure 6:
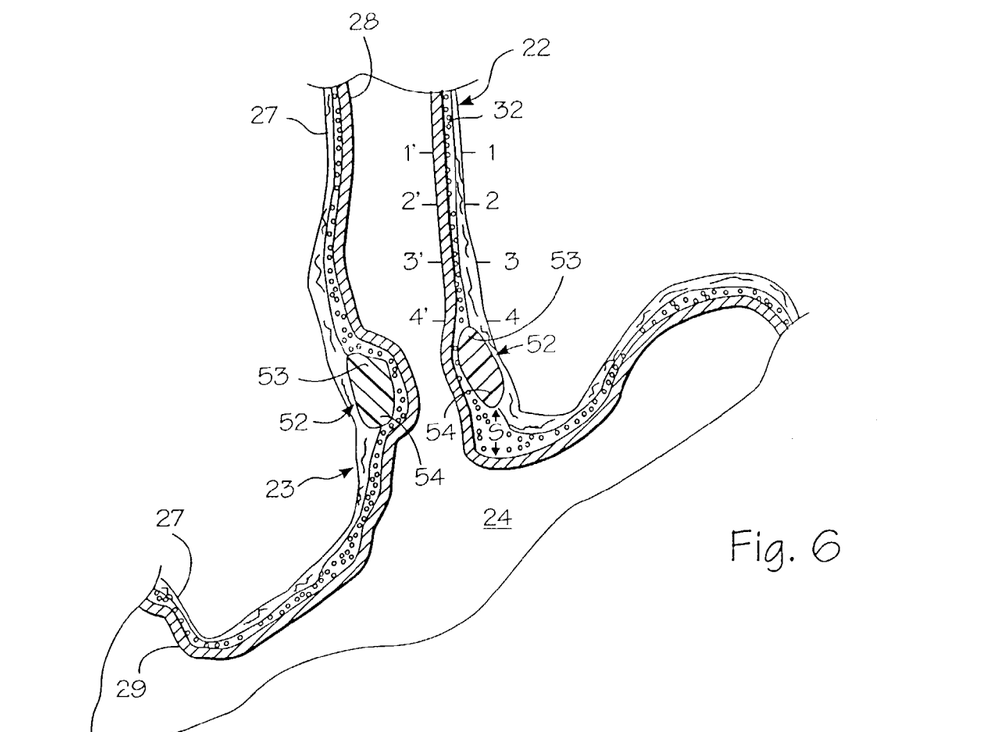
FIG. 6 is a schematic view of a cross section of the lower esophagus and non-distended stomach with implants demonstrating esophageal mucosal and esophageal muscle layers in register with one another.
Figure 7:
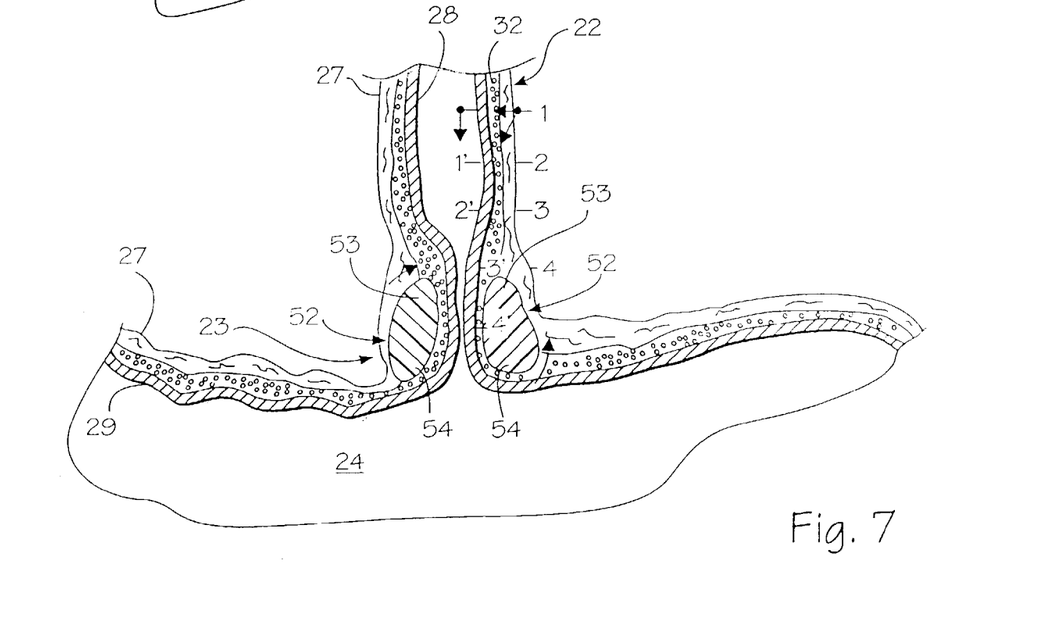
FIG. 7 is a schematic view similar to FIG. 6 in which the stomach is distended and wherein the implants are functioning as a valve-like mechanism.

The implantation of non-degradable or other materials in the esophageal sphincter 23 can form a structure which functions as an enhanced valve by at least two mechanisms occurring individually or concurrently. First, implants 52 formed and placed in appropriate positions within lower esophagus 22 at the level or in the vicinity of lower esophageal sphincter 23, preferably within either muscle layer 32 or 33, reduce the distensibility of esophageal sphincter 23. In FIGS. 3 and 6, stomach 24 is shown after placement of two or more implants 52 and preferably a plurality of circumferentially disposed implants in muscular layer 32 s shown in FIG. 4. Expansion of stomach 24 causes esophagus 22 to shorten as hereinbefore discussed with the result that the space between implant 52 and the cardia of stomach 24, identified by the reference S in FIG. 6, also begins to shorten. As stomach 24 distends further space S is further reduced as seen in FIGS. 5 and 7.

Distension of stomach 24 causes flexible mucosal layer 28 of esophagus 22 to move longitudinally or stretch and slide into stomach 24 relative to outer muscular layers 32 and 33 of esophagus 22. An analogy can be made to pulling the lining of a coat sleeve inside out relative to the outer shell of the coat arm. The result is that esophageal mucosal surface 28 moves downwardly towards stomach 24 more than esophageal muscular layers 32 and 33 as can be seen by comparing FIGS. 6 and 7. In FIG. 6, reference points 1', 2', 3' and 4' of mucosa 28 and corresponding reference points 1, 2, 3 and 4 of muscular layers 32 and 33 are respectively aligned or in register with one another. With greater distention as illustrated in FIG. 7, reference points 1', 2', 3' and 4' have moved downwardly relative to, and are out of register with, the corresponding reference points 1, 2, 3 and 4. This downward translation is also represented by arrows leading from the reference point 1 to the reference point 1'.

The downward movement of mucosa 28 relative to muscular layers 32 and 33 results in a two-fold effect. One, the esophageal mucosa 28 is further and more tightly apposed in the vicinity of lower esophageal sphincter 23, in particularly cephalad or superiorly to the sphincters 23. Tighter apposition is a result of the tightening and, hence, shortening of the mucosa 28 along the longitudinal axis of esophagus 22. In addition, due to the structure and orientation of the implants 52, downward longitudinal movement of mucosa 28 results in a downward and inward rotation of superior portions or poles 53 of implants 52 relative to inferior poles 54 of implants 52 towards mucosa 28 which, in turn, draws or pulls inwardly muscular walls 32 and 33 of esophagus 22. Together, these two effects significantly enhance the valve-like function or mechanism of implants 52 by inhibiting opening of esophagus 22 at lower esophageal sphincter 23 and creating a valve that is more competent than one created by merely bulking the esophageal sphincter with injections.

The optional contrast agent in the implants permits the implants to be monitored after completion of the procedure described above. Thus the stability of the implant and its configuration can be observed over time. Further procedures can be performed to supplement previously formed implants. It should be appreciated that the implants of the present invention can be used as delivery vehicles for other materials such as radio-isotopes, chemotherapeutic agents, anti-inflammatory agents and/or antibiotics.

The numerical sizes and ranges in the foregoing drawings are merely exemplary and not intended to be limiting of the purview of the invention. In addition, it should be appreciated that although four spherical implants are shown in the figures, one or a plurality of implants of various sizes and shapes may be suitably formed and positioned in the esophagus, in one or both of the circular and longitudinal muscle layers or sub-mucosally. A plurality of implants may also be disposed in more than one plane and still be within the purview of the present invention so long as they function together as a valve-like mechanism in the vicinity of the gastro-esophageal junction to prevent gastro-esophageal reflux during increasing distension of the stomach and resultant shortening of the esophagus.

Although the method of the invention has been described as including the formation of a space by a saline solution injected into the wall 27 prior to an injection of implant forming solution into the wall 27, it should be appreciated that the space can be formed by other aqueous or physiologic solutions or by a local anesthetic. Alternatively, the implant forming solution can be injected into wall 27 without the prior formation of a space by an injection of saline solution or otherwise. A saline or other aqueous or physiologic solution can optionally be introduced into such a space formed by the implant forming solution, that is after the introduction of the implant forming solution into the wall 27, to facilitate dispersion of the DMSO or other biocompatible solvent present in the implant forming solution. It should be further appreciated that the invention is broad enough to cover the introduction of an implant forming solution into wall 27 without the prior or subsequent introduction of a saline or other aqueous solution into the wall 27.

The invention encompasses the creation of a valve or valve-like structure or mechanism between other chambers in the gastrointestinal tract in order to increase or improve the competency of a sphincter between such chambers. Thus, where distension, increased pressure or a change in anatomy in a distal or second gastrointestinal chamber results in increased reflux into the first or proximal chamber due to a partially incompetent sphincter, such as anywhere in a lumen or passageway of a body of a mammal, creation of the valve-like structure will cause the mucosal layer to appose superior of the valve-like structure thereby lessening reflux from the second chamber into the first chamber. The method is particularly suited to creating a valve in order to supplement or replace a natural valve of a body. The method is also applicable to and suitable for a single chamber extending to a sphincter where the function and integrity of the chamber depends on the competency of the sphincter, such as the rectum, anus and the anal sphincter. For example rectal incontinence can be treated with this method.

Figure 8:
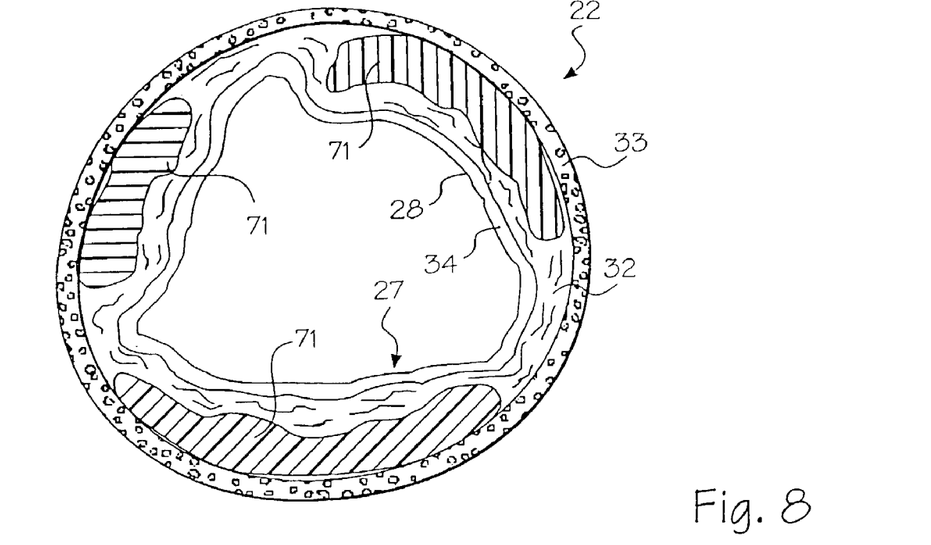
FIG. 8 is a cross-sectional view, similar to FIG. 4, of the wall forming the lower portion of the esophagus with a plurality of arcuate implants formed therein.
Figure 9:
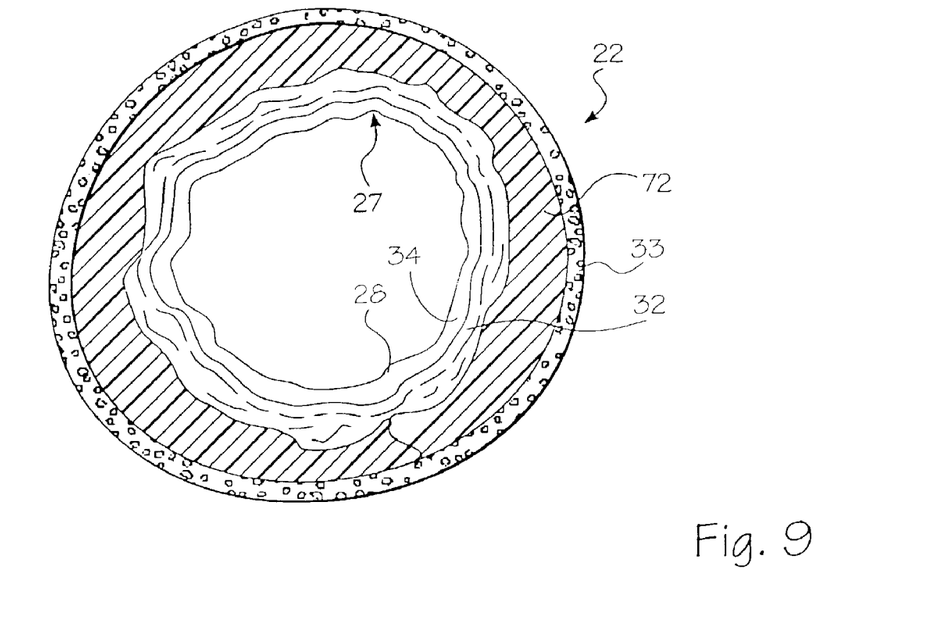
FIG. 9 is a cross-sectional view, similar to FIG. 8, of the wall forming the lower portion of the esophagus with a ring-like implant formed therein.

In another method of the present invention, one or more arcuate implants can be formed in a wall forming a natural body passageway within a body for augmenting the wall, for creating a valve-like mechanism or for any other purpose. Such arcuate implants could, for example, be formed in the vicinity of a sphincter such as the lower esophageal sphincter or the anal sphincter for the purpose of augmenting the sphincter or some other purpose. As a further example, such arcuate implants can be formed to create a valve-like mechanism or structure in the vicinity of a sphincter in such wall. In one specific example, one or more arcuate implants 71 are formed in wall 27 in the vicinity of lower esophageal sphincter 23 and more specifically at any of the locations discussed above (see FIG. 8). The implants 71 are preferably formed in one or both of muscle layers 32 and 33 and more preferably between the muscle layers 32 and 33. The arcuate implants 71 extend circumferentially around at least a portion of the wall 27. The implants can subtend an angle of less than 360° and more preferably less than 180°, as shown in FIG. 8, or can extend around substantially the entire esophagus so as to be ring-like or a ring, as shown in FIG. 9 with respect to ring implant 72.

Implants 71 and 72 are formed in substantially the manner discussed above and can be made from any of the materials discussed above. When the implants are formed from a solution, and preferably the nonaqueous solution comprised of a biocompatible polymer and a biocompatible solvent discussed above, the implant-forming solution can be introduced into the wall in any suitable way such as by means of a needle. The needle is introduced into one of muscle layers 32 or 33 and the implant-forming solution is then supplied to the needle. When it is desired to form the implants between the muscle layers 32 and 33, the needle can be moved or jiggled inwardly and/or outwardly during the injection process until the solution starts extending around the wall 27 and the passageway formed thereby to form an arcuate implant. The jiggling of the needle enhances dissection of the muscle layers 32 and 33 and facilitates introduction of the solution between these muscle layers. Once the muscle layers have been so dissected and implant-forming solution continued to be introduced, the solution has a tendency to extend around the wall as opposed to longitudinally up or down the wall 27. A ring implant can be continuous or have ends which abut, as in FIG. 9 with respect to implant 72. The injection needle is thus typically at the beginning or end of the arcuate implant.

The implants 71 and 72 can serve to augment or bulk wall 27 in the vicinity of lower esophageal sphincter 23, as discussed in U.S. Pat. No. 6,251,063, and/or can serve to form a valve-like mechanism in the manner discussed above. Ring implant 72 can further serve as a Angelchik-type prosthesis that is internal of wall 27 for inhibiting reflux from stomach 24.

Other suitable materials can be utilized for implant formation in the method of the present invention. Such materials include suitable suspensions such as injectable bioglass of the type described in Walker et al., "Injectable Bioglass as a Potential Substitute for Injectable Polytetrafluorethylene Particles", J. Urol., 148:645–7, 1992, small particle species such as polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 to Berg and biocompatible compositions comprising carbon coated beads such as disclosed in U.S. Pat. No. 5,451,406 to Lawin. Such suitable materials for forming implants further include collagen and other biodegradable material of the type disclosed in U.S. Pat. No. 4,803,075 to Wallace et al. and other known injectable materials.

From the foregoing it can be seen that a method for creating a valve-like mechanism in a natural body passageway has been provided. In such method, at least one implant is formed in the wall forming the natural body passageway and such at least one implant can include a plurality of circumferentially disposed implants. The one or more implants can include an arcuate implant extending circumferentially around at least a portion of the natural body passageway. The arcuate implant can be a ring-like implant. The method of the invention can be utilized to enhance the lower esophageal sphincter. More specifically, the formation of valve-like implants in the esophageal wall in the vicinity of the lower esophageal sphincter enhances the competency of the lower esophageal sphincter helping to prevent gastroesophageal reflux.

What is claimed is:

1. A method for creating an implant in a wall forming a cavity in a mammalian body and having a muscle layer extending circumferentially around the cavity comprising introducing a solution into the wall and forming a nonbiodegradable solid from the solution that extends along the muscle layer to form an implant in the wall.

2. The method of claim 1 wherein the implant is ring-shaped.

3. The method of claim 1 wherein the implant is arcuate in shape.

4. The method of claim 1 wherein the introducing step includes precipitating an implant from the solution.

5. The method of claim 1 further comprising a contrast agent in the solution for facilitating visualization of the implant in the wall.

6. The method of claim 5 wherein the contrast agent is suspended in the solution.

7. A method for increasing the competency of a sphincter in a gastrointestinal tract having a chamber extending to the sphincter, the chamber having a pressure therein and being defined by a wall having a muscle layer and a mucosal layer, comprising introducing a solution into the muscle layer in the vicinity of the sphincter and forming from the solution an implant in the muscle layer so as to create a valve-like mechanism in the wall, an increase of the pressure in the chamber causing the mucosal layer to appose in the vicinity of the valve-like mechanism so as to lessen the incompetence of the sphincter.

8. The method of claim 7 wherein the solution includes a biocompatible polymer and a biocompatible solvent.

9. The method of claim 8 wherein the solution includes a contrast agent.

10. The method of claim 8 wherein the solution of the biocompatible polymer and the biocompatible solvent has a composition comprising from about 2.5 to about 8.0 weight percent of a biocompatible polymer, from about 10 to about 40 weight percent of a water insoluble biocompatible contrast agent and from about 52 to about 87.5 weight percent of a biocompatible solvent.

11. The method of claim 7 wherein the solution includes a prepolymer and wherein the forming step includes polymerizing the prepolymer in situ to form an implant in the wall.

12. The method of claim 7 wherein the forming step includes precipitating an implant from the solution.

13. A method for increasing the competency of a sphincter in a gastrointestinal tract having a chamber extending to the sphincter, the chamber having a pressure therein and being defined by a wall having a mucosal layer, comprising introducing a biocompatible prepolymer into the wall in the vicinity of the sphincter and polymerizing the biocompatible prepolymer in situ to form an implant in the wall so as to create a valve-like mechanism in the wall, an increase of the pressure in the chamber causing the mucosal layer to appose in the vicinity of the valve-like mechanism so as to lessen the incompetence of the sphincter.

14. The method of claim 13 wherein the wall has a muscle layer and wherein the introducing step includes introducing the biocompatible prepolymer into the muscle layer of the wall.

15. The method of claim 13 wherein the introducing step includes introducing the biocompatible prepolymer into the wall beneath the mucosal layer.

16. The method of claim 13 wherein the wall has a submucosal layer and wherein the introducing step includes introducing the biocompatible prepolymer into the wall beneath the submucosal layer.

17. The method of claim 13 wherein the biocompatible prepolymer is part of a composition having a biocompatible solvent.

18. The method of claim 13 wherein the biocompatible prepolymer is part of a composition having a contrast agent for facilitating visualization of the implant in the wall.

19. The method of claim 13 wherein the introducing step includes extending a needle from the gastrointestinal tract into the wall and supplying the biocompatible prepolymer through the needle into the wall.

* * * * *